Figure 1:
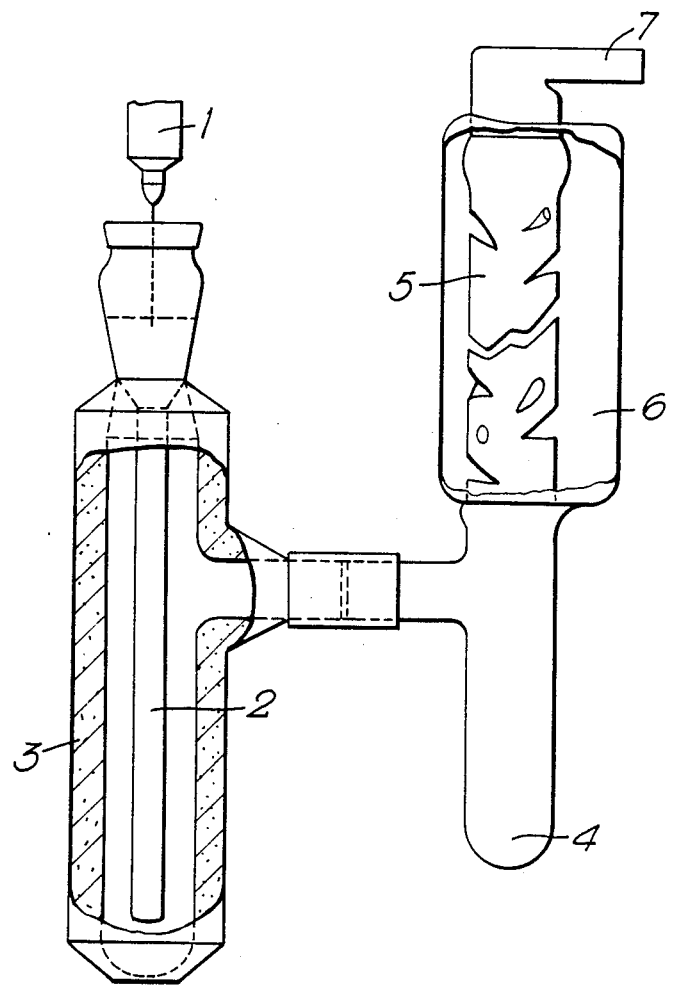

United States Patent [19]

Massonneau et al.

[11] Patent Number: 4,924,007
[45] Date of Patent: May 8, 1990

[54] PROCESS FOR THE PREPARATION OF CYCLIC SULPHATES

[75] Inventors: Viviane Massonneau; Michel Mulhauser, both of Ecully, France

[73] Assignee: Rhone-Poulenc Sante, Antony, France

[21] Appl. No.: 351,831

[22] Filed: May 15, 1989

[30] Foreign Application Priority Data

May 16, 1988 [FR] France ................. 88 06523

[51] Int. Cl.$^5$ ................ C07D 327/10; C07B 41/04
[52] U.S. Cl. ........................... 549/18; 549/34
[58] Field of Search ..................... 549/18, 34

[56] References Cited

FOREIGN PATENT DOCUMENTS 1171347 2/1958 France .

OTHER PUBLICATIONS

Lictenberger et al., *Bull. Soc. Chim.* (France), 1948, pp. 1002–1012.

*Primary Examiner*—Mary C. Lee
*Assistant Examiner*—M. S. Howard
*Attorney, Agent, or Firm*—Stevens, Davis, Miller & Mosher

[57] ABSTRACT

Cyclic sulphates of formula

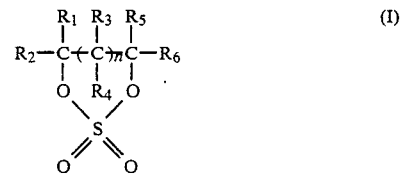

in which $R_1$, $R_2$, $R_3$, $R_4$, $R_5$, and $R_6$, which are identical or different, each denote hydrogen, halogen, alkyl, alkoxy, aryloxy or alkoxycarbonyl and n is 0 or 1, are prepared by rapid reaction, at a temperature of 150° to 250° C., of concentrated sulphuric acid with a glycol of formula 6 Claims, 1 Drawing Sheet

PROCESS FOR THE PREPARATION OF CYCLIC SULPHATES

The present invention relates to the preparation of cyclic sulphates of general formula:

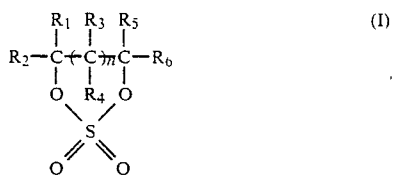

in which the substituents $R_1$, $R_2$, $R_3$, $R_4$, $R_5$ and $R_6$, which are identical or different, denote a hydrogen or halogen atom or an alkyl, aryl, alkoxy, aryloxy or alkoxycarbonyl radical and n is equal to 0 or 1.

In what precedes and what follows it is understood:
that the alkyl radicals and the alkyl moieties of the alkoxy or alkoxycarbonyl radicals contain 1 to 4 carbon atoms each and may be optionally substituted by one or more identical or different atoms or radicals chosen from halogen atoms and alkoxy, aryloxy or alkoxycarbonyl radicals,
that the aryl radicals and the aryl moieties of the aryloxy radicals contain 6 to 10 carbon atoms each and may be optionally substituted by one or more identical or different atoms or radicals chosen from halogen atoms and alkyl, alkoxy, aryloxy or alkoxycarbonyl radicals.

More particularly, the present invention relates to the preparation of cyclic sulphates of general formula (I) in which n is equal to 0 or 1 and the symbols $R_1$, $R_2$, $R_3$, $R_4$, $R_5$ and $R_6$, which are identical or different, denote a hydrogen atom or an alkyl radical.

The sulphates of general formula (I) are intermediates which can be employed in organic chemistry, in particular to perform hydroxyethylation reactions.

According to German Patent DE No. 1,049,870 it is known to prepare ethylene sulphate by heating a mixture of ethylene glycol, sulphuric acid and an excess of thionyl chloride under reflux for 50 hours.

It is also known, according to J. Lichtenberger and R. Lichtenberger, Bull. Soc. Chim. (France), 1002 (1948) to prepare cyclic sulphates of diols by reaction of an oleum with a chloroform solution of the diol, using at least two moles of free $SO_3$ per mole of diol, the oleum having a concentration of 47% of $SO_3$. However, while this method is suitable for primary-secondary diols, it does not work in the case of ethylene glycol.

It has now been found, and this is what forms the subject matter of the present invention, that cyclic sulphates of general formula (I) may be obtained by a simple and inexpensive process which consists in rapidly reacting, at a temperature of between 150° and 250° C., concentrated sulphuric acid with a glycol of general formula:

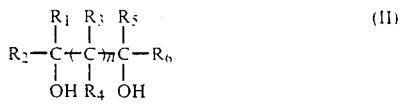

in which $R_1$, $R_2$, $R_3$, $R_4$, $R_5$, $R_6$ and n are defined as above.

In the new process the glycol of formula II and the concentrated sulphuric acid in the liquid or, preferably, the vapour phase are kept in contact at the reaction temperature in the range 150° to 250° C. for no more than one hour, preferably from less than 1 second to 30 minutes.

The cyclic sulphate of general formula (I) is trapped by cooling (i.e. by condensation from the vapour phase) or by dissolving it in a suitable solvent.

A substantially equimolar mixture of glycol of general formula (II) and of concentrated sulphuric acid is generally employed.

The process is preferably carried out under a reduced pressure, generally in the region of 1 mm Hg (0.13 kPa), and in the vapour phase.

For example, the process may be carried out by rapidly passing the mixture of concentrated sulphuric acid and of glycol of general formula (II) through a tubular reactor heated to a temperature of between 150° and 250° C. and kept under reduced pressure.

It may be advantageous to convey the mixture of reactants using an inert carrier gas.

The following Example shows how the invention may be put into practice.

EXAMPLE

Ethylene glycol (6.2 g, 0.1 mole) and 97% sulphuric acid (9.8 g, 0.097 mole) are mixed.

The mixture (2.5 g) is introduced with a syringe into the reactor shown in the accompanying FIG. 1.

The reactor is heated to 200° C. by means of a heating tape. The apparatus is placed under a reduced pressure of 1 mm Hg (0.13 kPa). The residence time of the ethylene glycol sulphuric acid mixture in the heated part of the reactor is 10 minutes.

The ethylene sulphate formed is collected in the Vigreux column placed in a jacket containing solid $CO_2$. When the reaction is finished, the Vigreux column is rinsed with dichloromethane. After the solution obtained has been separated and the dichloromethane evaporated, ethylene sulphate (0.85 g) is obtained in the form of white crystals. The yield is 45% based on the sulphuric acid employed.

In FIG. 1:
(1) shows the orifice for introducing the reactants;
(2) shows a reactant flow tube;
(3) shows a heating tape;
(4) shows the receiver for collecting the ethylene sulphate after rinsing of the Vigreux column;
(5) shows a Vigreux column;
(6) shows a cooling jacket; and
(7) shows the vacuum adaptor.

We claim:
1. A process for the preparation of a cyclic sulphate of formula:

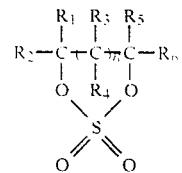

in which $R_1$, $R_2$, $R_3$, $R_4$, $R_5$ and $R_6$, which are identical or different, each denote a hydrogen or halogen atom or an alkyl, aryl, alkoxy, aryloxy or alkoxycarbonyl radical and n is 0 or 1, the aforesaid alkyl radicals and the alkyl moieties of the alkoxy and alkoxycarbonyl radicals containing 1 to 4 carbon atoms each and being unsubstituted or substituted by one or more identical or different atoms or radicals chosen from halogen atoms and alkoxy, aryloxy or alkoxycarbonyl radicals, and the said aryl radicals and aryloxy radicals containing 6 to 10 carbon atoms each and being unsubstituted or substituted by one or more identical or different atoms or radicals chosen from halogen atoms and alkyl, alkoxy, aryloxy or alkoxycarbonyl radicals, and n is 0 or 1, which comprises reacting concentrated sulphuric acid rapidly at a temperature of 150° to 250° C., with a glycol of formula:

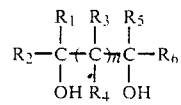

in which $R_1$, $R_2$, $R_3$, $R_4$, $R_5$, $R_6$ and n are as defined above, and recovering the cyclic sulphate obtained.

2. A process according to claim 1 in which $R_1$, $R_2$, $R_3$, $R_4$, $R_5$ and $R_6$, which are identical or different, each denote a hydrogen atom or an alkyl radical and n is 0 or 1.

3. Process according to claim 1, wherein a substantially equimolar mixture of the glycol and of concentrated sulphuric acid is used.

4. Process according to claim 1, wherein the reaction is carried out under reduced pressure.

5. Process according to claim 4, wherein the reaction is carried out at about 1 mm Hg or 0.13 kPa.

6. Process according to claim 1, wherein the reaction is effected in the vapour phase and the mixture of the glycol and sulphuric acid is diluted with an inert gas.

* * * * *